United States Patent [19]

Sharples

[11] 4,106,671
[45] Aug. 15, 1978

[54] LIQUID HEAD CONTROL SYSTEM

[75] Inventor: Thomas Davy Sharples, Atherton, Calif.

[73] Assignee: Beckman Instruments, Inc., Fullerton, Calif.

[21] Appl. No.: 779,379

[22] Filed: Mar. 21, 1977

Related U.S. Application Data

[63] Continuation of Ser. No. 627,804, Oct. 31, 1975, abandoned.

[51] Int. Cl.² .................................. B67D 5/54
[52] U.S. Cl. .............................. 222/61; 222/64; 222/399; 250/577; 137/386
[58] Field of Search .............. 222/52, 56, 61, 64, 222/69, 394, 396, 399, 1, 14, 66, 67, 68; 137/209, 386; 250/577

[56] References Cited

U.S. PATENT DOCUMENTS

| 2,083,965 | 6/1937 | Schulz | 222/61 |
| 2,520,175 | 8/1950 | Socke | 222/61 |
| 3,194,434 | 7/1965 | Evanson | 222/399 X |
| 3,504,825 | 4/1970 | Diamond et al. | 222/396 X |
| 3,664,549 | 5/1972 | Maselli | 222/64 |

*Primary Examiner*—Robert B. Reeves
*Assistant Examiner*—Joseph J. Rolla
*Attorney, Agent, or Firm*—Robert J. Steinmeyer; Robert S. Frieman

[57] ABSTRACT

An automatically controlled liquid dispensing system including a reagent dispenser adapted to function as an intermediate container for dispensing relatively small controlled volumes of liquid to an associated receiving system in a continuous "demand" mode, this dispenser being indirectly monitored to be automatically and continually replenished after liquid is withdrawn therefrom, using a simple photoelectric liquid level monitor system including a fail-safe overflow control arrangement.

6 Claims, 3 Drawing Figures

LIQUID HEAD CONTROL SYSTEM

CROSS REFERENCES TO RELATED APPLICATIONS

This application is a continuation of Applicant's prior copending application, Ser. No. 627,804, filed Oct. 31, 1975, now abandoned.

FIELD OF THE INVENTION

This invention relates to liquid dispensing systems and more particularly to such systems adapted to automatically replenish dispensed liquid, indirectly monitoring the liquid level in a dispenser vessel and automatically acting on it responsive thereto.

BACKGROUND, FEATURES OF INVENTION

In connection with the employment of vestibule-valve refill arrangement (see U.S. patent application Ser. No. 627,803 filed on Oct. 31, 1975, now U.S. Pat. No. 4,029,473), it was discovered that commercially available pressure regulators of sufficient sensitivity and adequate control accuracy to refill a remote vestibule vessel to a desired level were very expensive. Furthermore, none available were at all suitable for reliable operation with a system required to handle reagents and solvents of corrosive and otherwise agressive characteristics.

The present invention is designed to circumvent the problem of expensive pressure regulators by measuring and controlling the liquid head in the supply vessel so as to thereby control the liquid fill level in a remote "vestibule vessel."

It is a further object of the present invention to accomplish the desired control with relatively inexpensive commercially available photoelectric detectors, solenoid valves, sample fittings and parts readily fabricated from materials, such as glass, which is appropriate for the liquids to be handled.

It is a further object to provide a closed liquid delivery system in which the reagents are protected from exposure to the atmosphere and in which the operating gas may be dry nitrogen or other inert dry gas.

Another object of the invention is to provide a system which is "fail-safe" against accidental overpressure or accidental failure of certain components such as incandescent lamps in the liquid detector devices.

More particularly, in systems according to the invention the liquid head at the reservoir vessel is monitored directly and conveniently with relatively simple inexpensive available equipment. Also, a malfunction detector and associated alarm is also readily provided for simply detecting "over-pressure" and "over-flow" conditions to responsively invoke an automatic alarm and "shut-down," as well as to vent the pneumatic drive system. The resulting system is relatively insensitive to rather wide variations in required driving gas pressure, requiring no special adjustments for various densities of transferred liquids, and is relatively insensitive to variations in ambient and supply pressure. Also, it will continue to supply reagent to a transfer vessel despite a relatively massive gas leakage from the system. Also, according to other features of the invention, such systems provide an immediate, and direct, indication of significant gas leakage from the system (e.g. from a supply vessel closure or from any of the gas delivery lines and associated seals).

Thus, it is an object of the present invention to provide at least some of the foregoing solutions and features of advantage in an improved liquid dispensing system. A related object is to provide such an improved system wherein liquid is transferred from a reservoir to a transfer vessel by pneumatic means operated automatically according to controls monitoring a liquid level directly related to the liquid level in this vessel. A related object is to provide such a system wherein automatic drive-pressure control is achieved via direct detection of this liquid level, rather than indirectly, such as by monitoring pressure.

A related object is to provide such a system using inexpensive, readily available liquid level detector means. Yet a further object is to provide such using an array of photosensor means adapted to detect the rising level of liquid in a riser tube communicating with a reservoir and wherein control means responsive to detected high liquid levels are adapted to vent the pneumatic drive-system in a controlled pulsed fashion.

Yet a further object is to provide such a system wherein an "over-flow" detect means is supplementarily provided and is adapted to detect extreme, "over-flow" levels of stored liquid and responsively relieve the pneumatic replenishment system in a "fail-safe" manner. A further object is to provide such a system and detector adapted to vent the supply reservoir and to disable all fill-operations until "reset."

These and other objects of the invention will become more apparent from the following description and appended claims, reference being made to the accompanying drawings forming a part of the specification.

IN THE DRAWINGS

While specific embodiments will now be described in detail and represent preferred embodiments of the present invention, it should be understood that this invention is not limited in application to the specific indicated details of construction and arrangement of parts, or to the associated techniques or modes of operation, or to what is illustrated in the accompanying drawings and described herein. Rather, the invention is capable of other embodiments and of being practiced in various other ways within the scope of the appended claims as recognized by those skilled in the art. Thus it is to be understood that the terminology employed herein is only for purpose of description and not of limitation; with the invention's scope being limited only by the appended claims.

Embodiment: in General

Figure 1:
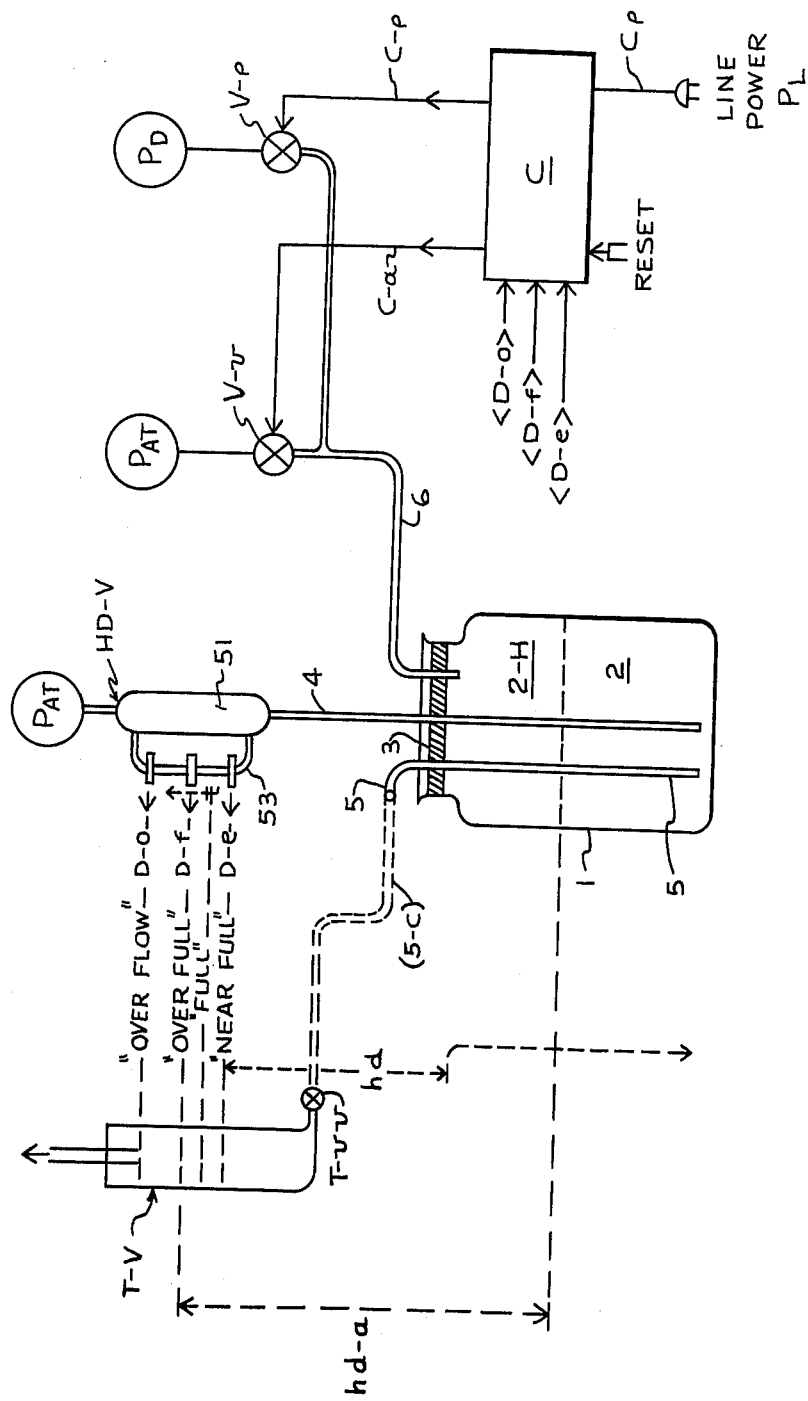
FIG. 1 is a diagrammatic view of one embodiment of the invention showing a supply vessel and an associated receiving vessel in conjunction with pneumatic drive means and associated controls, including liquid level detectors, adapted to automatically control the drive and other means.

The liquid dispensing and associated control apparatus in the embodiment in FIG. 1 will be understood as operating essentially upon a closed supply vessel, or reservoir 1. A pneumatic drive (pressurized transfer gas) system will be understood as applied (as known in the art) to supply vessel 1 to transfer certain liquid contents thereof into a receiving transfer vessel T-V.

The liquid delivery system will be understood to include a supply of pressurized gas (first pressurizing means) PD with an associated supply valve V-$p$ provided to control transfer of liquid 2 from the relatively large supply vessel 1, along a supply conduit 5-C and through a valve means T-$vv$ to replenish the liquid supply in transfer vessel T-V and in general, maintain it at a prescribed reference "full" level as indicated in FIG. 1. Thus, in conjunction with reservoir 1 and according to one feature of the invention, a direct liquid level monitor system HD is provided to monitor the head pressure in the supply vessel 1 and to generate control signals for invoking pneumatic (filling or venting) and other operations responsively. System HD includes a detector vessel HD-V provided with an array of liquid level detector units D-$o$, D-$f$, D-$e$ to detect presence or absence of liquid at respective monitoring levels in detector vessel HD-V that is, an extreme "overflow" detector D-$o$, an "over-fill" detector D-$f$ and a "near-full" detector D-$e$ positioned as indicated in FIG. 1.

In addition, a venting valve V-$v$ is provided to relieve pneumatic pressure in reservoir 1 together with an associated automatic control system C. Control system C is adapted to operate responsive to control signals from the mentioned level detectors and responsively manipulate the pressurizing and venting valves according to another feature hereof (more fully described below in association with FIG. 2). These level monitoring and associated control systems will thus be understood as generally operating to automatically maintain a pressure head in the supply vessel and thereby indirectly maintaining a reference level of liquid in transfer vessel T-V, as close to the "full" level as possible, using relatively inexpensive reliable simple means and avoiding such undesirable expensive expedients as fussy gas pressure regulators, etc.

Thus, the measurement of the pressure head in the supply vessel (via associated head-detect vessel HD-V, in hydraulic communication therewith) will be understood as detected to invoke the application of gas pressure to drive liquid from reservoir 1 to transfer vessel T-V. This will be seen as simplifying detection, since liquid position is relatively easy, simple and inexpensive to detect over a relatively wide range (as opposed to gas pressure). Also this arrangement will inherently compensate for such things as shifts in pneumatic or atmospheric pressure.

Prior Art

Now, workers in the art will recognize that for such a reservoir 1 using a pneumatic drive to maintain the level of liquid in transfer vessel T-V, it would be relatively conventional to replace the indicator liquid level detector system HD with a gas pressure detect system communicating with the gaseous atmosphere in reservoir head-space 2-H (above the level of liquid 2 in reservoir 1) adapted to monitor the gas pressure there to thereby — indirectly — control the level of liquid in vessel T-V. The pressure (above atmospheric) in vessel 1 will vary with this level and thus can be monitored and kept constant to automatically drive liquid into vessel T-V to — within certain limits — maintain the reference "FULL" level therein.

Workers in the art are fully familiar with the drawbacks in such systems, especially when (as in the instant case) the average head hd (difference in elevation between average level in vessel 1 and reference "full" levels in vessel T-V) is relatively large (here on the order of 12 to 16 inches, indicating a relatively wide excursion in monitored gas pressures). That is, pneumatic replenish-pressure will vary between a minimum corresponding to difference in "near-full" level in vessel T-V and a full level in supply vessel 1 at low atmospheric pressure) and a maximum corresponding to the difference between an "over-flow" level in T-V and a nearly empty supply vessel 1, at a relatively high atmospheric pressure ($P_{at}$, etc.). Workers realize that relatively expensive, complex pressure regulators and associated sensing means are necessary to provide the close regulation desired in such cases. Moreover, further expensive complex equipment is necessary too for "fail-safe" operation. Further, even under the best of conditions such arrangements will monitor only an "indirect" indication of liquid level as compared with the present invention. The invention avoids these difficulties, using simple, readily available expedients (e.g. no high-pressure detectors regulating or valves) to avoid high-pressure gear and prevent accidental delivery of excess reagent.

Details of Embodiment: FIG. 1

One embodiment of the invention shown in FIG. 1 will be understood as including the following particular details and as comprising an improved liquid dispensing control arrangement which may be advantageously employed in conjunction with a "vestibule-valve" refill arrangement described in companion, commonly owned U.S. patent application Ser. No. 627,803.

Reservoir 1 containing a reagent solution 2 of prescribed specific gravity will be understood as pressure-tight being fitted with a pressure-tight closure 3 through which passes a riser tube 4, a delivery tube 5, communicating with vessel T-V via conduit 5-C (shown in phantom) and a check valve T-$vv$, plus a pressurizing tube 6 for admitting pressurizing gas from source $P_D$ (adapted to control selective transfer of reagent 2 to vessel T-V) and for venting to atmosphere $P_{at}$.

According to a particular feature of the invention, riser 4 communicates with a level monitor arrangement HD, including a detect vessel HD-V and the three mentioned level sensor systems D-$o$, D-$f$, D-$e$ arrayed along a narrow bypass section 53 of vessel HD-V. Vessel HD-V also includes an enlarged sump portion 51 for accommodation of transient hydraulic surges as known in the art. These detectors may preferably be position-adjustable and function in a known manner to detect the presence or absence of liquid at their respective levels in tube 53 — those corresponding to the same liquid level in transfer vessel T-V which will be understood as in hydraulic communication with vessel HD-V for this purpose. In this embodiment the detectors are preferably photoelectric as further described below, including photocells basically adapted to detect the presence or absence of light at a respective site as admitted through liquid in tube 53, or alternatively as intercepted thereby, according to the selected control logic. As more fully explained below, and according to a principal feature of the invention, application of the various detector outputs to control unit C operates to responsively invoke replenishment operations and the like, such as admitting pressurized gas to reservoir 1 via valve V-$p$ while also closing vent V-$v$ sufficient to bring the liquid in vessel T-V up to, and beyond, the indicated "near-full" level;

and thereafter, upon a further rise in the liquid level to the indicated "over-full" level, operating to close valve V-$p$ and to open vent valve V-$v$ (preferably in a pulsating fashion) to reduce the driving gas pressure in reservoir "head-space" 2-H and thus drop the level in T-V to (eventually) come to rest close to the reference "FULL" level.

As workers in the art will readily appreciate, such a system provides one with relatively wide latitude for setting the "near-full" and "over-full" points at prescribed adjustable levels relative to the nominal "FULL" level, simply, such as by adjusting the positions of detectors D-$e$, D-$f$. Such a position-adjustment can also act to compensate for a certain "inertia" normally present in the hydraulic system. This compares favorably with a conventional gas-pressure monitoring arrangement which is usually at the mercy of such inertia effects.

That is, using prior art techniques, one would typically provide a pressure regulator to open the pressurizing valve V-$p$ when the pressure sensed at head space 2-H fell below a prescribed level corresponding to that at the "near-full" liquid level; then, a pneumatic fill operation would be invoked and maintained until pressure rose to a certain higher level corresponding to liquid at the "over-full" level, when it would be terminated. Further, one could invoke "venting" at this, or a higher ("over-flow"), pressure, corresponding to liquid at the higher "over-flow" level in T-V. But it will be recognized as relatively difficult and time-consuming to set and readjust the respective control pressures for this purpose. Also slight changes in service conditions such as in atmospheric pressure ($P_{at}$), or in the length of conduit 5-C, or the capacity of vessel T-V or reservoir 1, or in the size or type of valves used, will typically require readjustment of the reference pressure points. But no such readjustment is needed with the invention.

According to a preferred form of this invention, an "over-full" detector D-f is operative to vent reservoir head space 2-H in a prescribed pulsing fashion. That is, it has been discovered that typical commonly available solenoid-operated pressure gas valves will respond beautifully to (selectively adjustable) current pulses adapted and arranged to repeatedly thrust the valve to "partly-open" condition and oscillate it there — pulsingly — thus venting the system more slowly and gradually and providing a simple "fractional-throughput" control of valve throughput with time, where otherwise this is quite difficult and complex. That is, such solenoid valves do not lend themselves to being "partly opened" to a controlled degree as workers well know.

According to another preferred feature a third, "over-flow" detector D-$o$ is also provided to invoke an "Emergency-vent condition," i.e. to vent the system fully open to relieve pressure in 2-H and bring it down to atmospheric pressure as fast as possible, while also throwing appropriate alarms and disabling pressurizing (fill) valve V-$p$ until the system is "reset." This feature can also be used to render the detect system "fail-safe," being set to automatically invoke these emergency measures in the event of system failure and thereby avoiding resultant overfilling of vessel T-V. This "emergency" condition will prevail until control C is "RESET" as mentioned.

Figure 3:
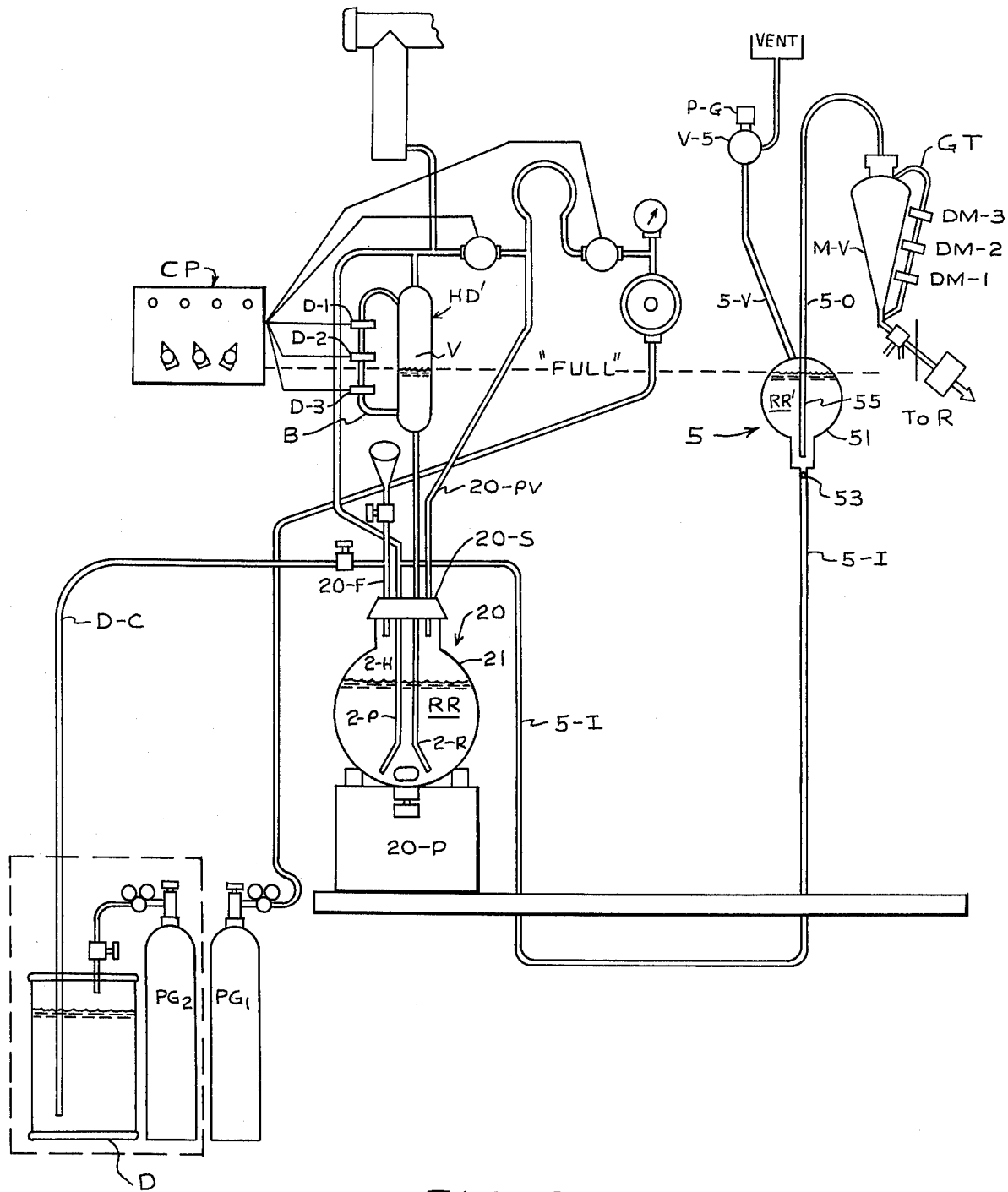
FIG. 3 is an illustrative showing of a modified embodiment like that of FIG. 1 in conjunction with details of a peptide synthesizer arrangement.

Using the invention with a peptide synthesizer embodiment like that of FIG. 3, with vessel T-V providing metered reagent delivery thereto, the invention has been observed to facilitate very efficient operation, with a relatively low "refill-time" — e.g. assuming a transfer vessel T-V of 250 ml capacity with a reservoir 1 of 5 liter capacity and about 25 feet of 8 mm tubing between vessels, for reagent 2 comprising a solvent like ethanol having a specific gravity of about 0.95. In this application, note that there is an approximate 20:1 ratio in capacity between the reservoir and the transfer vessel. Similar results have been achieved with reagent having up to about 1.5 specific gravity and using reservoir and transfer vessel capacities in the ratios of: 12 liters/1 liter, 20 liters/2 liters, and 48 liters/3 liters. This will emphasize the versatility and simple, precise control possible with the invention, while using simple, inexpensive implementation, as will be apparent to those skilled in the art, whether using the described or other equivalent systems.

Control Operations

The refill control logic is so arranged and associated with the detectors D, that the opening and closing of the solenoid valves V-$p$ and V-$v$ is automatically controlled by the control unit C to produce the mentioned results.

This control logic is so arranged that when no liquid is present in tube 53, sensor PC-$e$ and unit D-$e$ will issue a control signal S-$e$ to control unit C adapted to open pressure valve V-$p$ and pressurize the head space 2-H to drive reagent 2 out along conduit 5-C, as well as up riser 4 into tube 53, until the "near-full" level is attained and the liquid intercepts the detect axis at D-$e$. At this point, the signal will change (from $I_e$ to $\bar{I}_e$, see Table I) and release pressure valve V-$p$ to resume its normal "closed" condition (vent valve V-V being thewhile spring-retained in its normal closed condition). This gas drive would typically constitute air supplied at from a pressurized source operating at about 10–30 psi.

Now, depending upon the pressure in supply $P_D$, upon the condition and size of the orifice of valve V-P, upon the volume of head space 2-H in reservoir 1, and other variables (including atmospheric pressure $P_A$), the liquid level in T-V may override, rising beyond the "Full" level and up to the "overfull" level, to intercept the detect axis of detect system D-$f$. This generates a signal ("$I_f$") to, in turn, cause control C to open vent valve V-$v$, doing so in a "pulsating" fashion, and only sufficient to reduce the gas pressure at head 2-H so that the liquid level at T-V drops below "over-full" to come to rest closely adjacent the "Full" level.

Of course, if too much gas is vented through valve V-$v$, the liquid level will continue to drop below "FULL" (and also below "near-full" possibly), invoking, again the operation of sensor system D-$e$, and the above pressurizing (fill) cycle will be repeated. Thus, as with all such control systems, it is necessary to design and adjust these control elements so that the fill and vent modes do not oscillate; e.g. by so adjusting the magnitude and width of the current pulses to solenoid SL-2 and/or by adjusting the position of detector D-$f$ (with D-$f$ higher on HD-V the "equilibrium level" shall be thrown closer to "FULL").

Workers will recognize that such a control system can continually provide sufficient pneumatic drive at head space 2H to maintain the liquid level close to that desired ("FULL"), although there would be a certain amount of adjusting and optimization necessary usually. For instance, oscillation should be avoided to prevent unnecessary consumption of operating gas $P_D$, and associated losses of evaporating reagent plus wear and heating of the valves. But a principal feature of control systems according to this invention is that signals from "over-full" sensor D-$f$ are coverted to a pulse (or series of pulses, functioning to so operate the vent valve (solenoid) that, with appropriate adjustment of pulse width and rate, this oscillating mode may usually be avoided. Such adjustments can also accommodate changes in the system such as in reagent-gravity, or in the relative sizes and capacities of the vessels, or in the length and capacity of the connection-conduits, or in atmospheric pressure or supply pressure, etc. Indeed, when properly adjusted, any tendency of the control system to oscillate with frequent venting and pressurizing provides immediate indication that a gas or other leak has developed in the system.

Also the positions of sensors D-$e$ and D-$f$ may of course readily be made adjustable in a relatively simple manner to either change the sensitivity of the system and/or to shift the reference ("FULL") level thereof. Such adjustability, as further described below, is enhanced by providing electronic control means with a rather wide response range and adjustability, with adjustable pulse spacing and width (e.g. to accommodate different valve excursions), where desired pulse amplitude may be adjusted to accommodate different solenoid requirements, etc., as well.

In addition it has been found convenient to utilize the head detector arrangement indicated including a dip tube portion 4 coupled to detect vessel 51 including the "gauge glass," or narrow bypass tube 53, on which is mounted the liquid-sensing photodetect arrays.

DETECTORS

Figure 2:
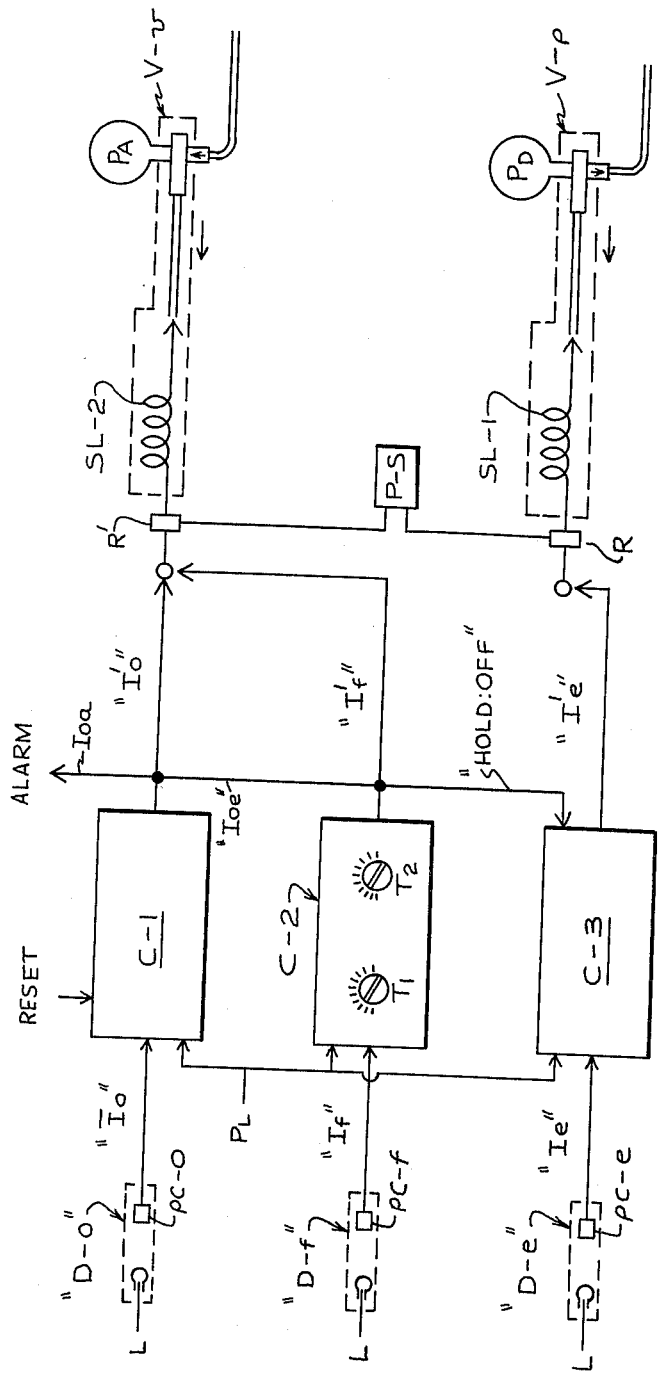
FIG. 2 is a diagrammatic view of the electronic and associated controls for the embodiment of FIG. 1 wherein various control signals are developed from liquid level monitoring sensor systems.

FIG. 2 indicates, in schematic block diagram fashion, a preferred mode for implementing the above-indicated detect system whereby signals emanating from detectors D-$o$, D-$f$ and D-$e$ are manipulated to operate the solenoid valves V-$p$, V-$v$, and other associated means. The respective states of these detectors, the conditions they respond to and the operations and results they effect are indicated summarly in Table I below which may be best read in conjunction with FIGS. 1 and 2:

as well known by those skilled in the art. Preferably, light sources L comprise incandescent lamps energized as known in the art, each arranged in operative association with a respective photocell PC. Thus, according to a preferred feature hereof and as indicated in Table I, "near-full" detect cell PC-$e$ provides its operative signal when its detect axis is not intercepted by liquid (in tube 53), whereas the other detectors (see Table I) PC-$f$, PC-$o$ operate in a reverse logic sense to provide an operative output signal only when their detect axis is intercepted by such liquids. Additionally, with "overflow" detector PC-$o$, the cell output normally operates to inhibit its associated driver C-1 thus preventing output therefrom unless and until its detect axis (light to photocell) is intercepted by the liquid, in which case the cell goes "dark," allowing driver C-1 to "go high" and so throw open the vent, activate the alarm and disable "fill driver" C-3 until reset.

Thus, in FIG. 2 a "no light" output $\bar{I}_o$ will be understood to indicate that the "normal " output $I_o$ from cell PC-$o$ is adapted to inhibit associated driver C-1 until it is removed (i.e. when signal $\bar{I}_o$ appears), whereupon C-1 will begin to emit operating signals $I'_o$, $I_{oa}$, $I_{oe}$ — this when the illuminating light beam is deflected away from cell PC-$o$ by intervening light in gauge tube 53 (otherwise PC-$o$ will continue to inhibit C-1 output by application of signal $I_o$ indicating "no liquid" at the "over-flow" level.

More particularly, upon disappearance of output from cell PC-$o$, driver C-1 will begin to supply a (continuous, full-vent) signal $I'_o$ to relay R' (FIG. 2) to thereby energize vent solenoid SL-2 (via power source P-S) and pull vent valve V-$v$ fully open, and hold it so, when liquid rises to the level of sensor D-$o$ or if there is any failure in the lamp or other portions of this sensor. Power supply P-S is preferably designed to energize both two solenoid operated valves in a two-step mode providing an initial current surge, high enough to cause reliable full valve actuation and unseating, followed by a reduced "hold voltage" for maintaining the valve so-actuated, without overheating or excessive use of power as known in the art. Of course, workers will

TABLE I (See FIGS. 1, 2)*

| Detector Unit | Signal | Condition of Vessel HD-V | Liquid Intercept in HSD-V? (pH-Cell Axis) | Activates | Output | Operations | Result at Vessel 1 |
|---|---|---|---|---|---|---|---|
| PC-e | $I_e$ | "Not full" | No | C-3 | $I'_e$ | Hold V-p OPEN (i.e. to pressurize 2-H, pump from 1 into T-V) | FILL |
|  | ($\bar{I}_e$) | "Near-full" | Yes | None | None | C-3 inactive; V-p released to CLOSE | STOP-FILL |
| PC-f | $I_f$ | "Over-full" | yes | C-2 | $I'_f$ OPEN V-v to vent | | PULSE- |
|  |  |  |  |  |  | in pulsed fashion (see FIG. 3) | VENT |
| PC-o | $I_o$ | "No over-flow" | No | inhibits C-1 | None | — | — |
|  | $\bar{I}_o$ | "Over-flow" or "pH-det.sys.FAILED" (e.g. PC-o inoper.) | Yes | enables C-1 | $I'_o$ — $I_{oa}$ — $I_{oe}$ — | throw V-p fully OPEN activate alarm hold C-3 disabled — only "RESET" restores | FULL VENT, ALARM PREVENT- FILL |

*assume valves V-p, V-v are solenoid-operated, held "normally CLOSED" (e.g. by spring)
*Note: $\bar{I}_e$ indicates absence of $I_e$ signal and/or presence of contrary signal Thus it will be understood that the photodetect units D-$o$, D-$f$ and D-$e$ preferably include light sources L and associated photocells PC coupled to activate associated drive control stages C-1, C-2, C-3, respectively, these drive stages providing output control signals adapted to control the condition of the (valve) solenoids and of other control means in the manner indicated above and recognize that the same, or similar, means as described above may be differently employed to effect different analogous operations.

This results, of course, in a "fail-safe" system as workers will appreciate, in that failure in the lamp or other detect system component will result in automatic shutdown, just as in the case of an "over-flow" condition.

The fail-safe operation of D-*o* not only protects the failure of its own system, but also protects the D-*f* and D-*e* systems, the failure of which may produce over-filling and/or over-pressurization.

"Near-full" detect cell PC-*e*, on the other hand, is designed to control associated driver C-3 to deliver power (from source P-S) to pressurizing valve solenoid SL-1 (via relay R) and so hold valve V-*p* open to pressurize reservoir 1 until liquid appears at this "near-full" level in gauge tube 53 whereupon valve V-*p* will be disabled by interruption of power to SL-1 and the valve allowed to be spring-returned to its normal, closed condition. Thus appearance of liquid in the gauge glass at "near-full" level (the level set by the positioning of sensor D-*e*, as indicated above) automatically terminates the fill operation. As workers in the art realize, this liquid diverts lamp illumination away from cell PC-*e* so that its output $I_e$ to drive stage C-3 enable the C-3 output $I'_e$ switch relay R to energize solenoid SL-1 to "open" condition.

Of course reverse logic may be used to the same end, with any of these level sensor units, e.g. whereby the photocell output will be applied to open a normally closed switch means and thereby interrupt power to a valve solenoid.

Driver C-2, according to a preferred form of the invention, supplies pulsed power (signals $I'_p$) to vent valve solenoid SL-2 as indicated above (from source P-S via relay R') when liquid appears in gauge 53 to intercept its ("over-fill") detect axis at the level set by positioning of sensor D-*f*. The spacing (frequency) and width of the solenoid pulses are preferably made adjustable according to controls $T_1$ and $T_2$, or otherwise implemented for "pulsing control" as understood in the art. This, in effect, conveniently delivers, with each pulse a prescribed relatively high current pulse to "start" the solenoid moving (sufficient to pull the valve to a prescribed (partly, or fully) "open" condition (this being determined according to pulse amplitude) with this pulse being prolonged for a prescribed time ("open-period" set by pulse-width adjustment) and at a rate which is adjustably set to derive a given fraction of "full-venting." With a typical solenoid valve this is simpler than attempting any steady-state controlled partial-opening of the valve.

In this fashion, and as understood in the art, the pulse rate and width — approximating the power delivered to solenoid SL-2 — may be adjusted to control the frequency and duration of each opening of the vent valve so that, in effect, gas is vented from the delivery system at a prescribed rate which is adjustable (i.e. rate of dropping pressure in space 2-H of reservoir 1). For instance, in the subject system, using capacitive power storage, it has been found that the pulse width may be varied from 9 to 62 milliseconds approximately with inter pulse spacing on the order of 0.7 to 8 ms. for the indicated embodiment.

Moreover, as workers will appreciate, in certain instances it will be advantageous to similarly pulse the opening of pressurizing valve V-*p* prior to detection of liquid at detector D-*e* so as to provide a variable control on the rate of (volume of) pressurized gas injected into space 2-H, rather than attempt to adjust the degree of solenoid-opening (something usually unpractical, as workers know). Now, of course, in either case this pressurizing may be other than in a pulsating fashion. However, it has been found that provision of a pulsating burst as opposed to a single massive burst both allows one to more carefully and simply meter and adjust the rate of gas through-put in a solenoid valve as well as to decelerate the rate at which this occurs so as to smooth out a massive surge along the hydraulic (and liquid) lines and allow the system to equilibrate more readily and without undue oscillation.

Other supplemental level detection systems could also be used, for instance one located just below the "near-full" level to be operated in tandem with system D-*f* for beginning the opening of valve V-*v* in a (slower) pulsating fashion. Detector D-*e* could complete this job by opening the valve more fully and at a faster rate as necessary. Such a gradual closing mode could slow down the rate at which the rising liquid level in vessel T-V approaches its nominal "full" value and minimize overrun and oscillations as mentioned.

Of course these photodetect systems can be operated equally well at a "normally on" or a "normally off" mode, together with suitable control logic responsive thereto, so that the interception of their detect axis by liquid can either stimulate, or terminate, a control output signal therefrom, as workers will appreciate.

Modified Embodiment — FIG. 3:

FIG. 3 illustrates still another embodiment, being approximately the same in construction and operation to that shown in FIG. 1, and a described, above except where otherwise stated. This embodiment is shown in conjunction with details of the associated pneumatic liquid delivery arrangements and associated control means, plus various other incidents in a typical peptide synthesizer application.

More particularly here, the reservoir, or storage arrangement 20 will be understood as comprising a relatively massive storage flask 21 mounted on a pedestal 20-P and including an orifice sealed by appropriate sealing means 20-S through which are introduced a level control riser 2-R, an outlet riser 2-P, and a pressure-vent tube 20-PV. Tube 20-PV is connected, through appropriate valves and a pressure reducer, to a source of pressurized gas PG-1 and is adapted to expel reagent RR. Level control riser tube 2-R is provided to transfer stored reagent RR up to level detect unit HD', while outlet riser 2-P is adapted to pass liquid along a prescribed conduit 5-I for admission, through a ball-check valve 53, to a vestibule arrangement 5. Vestibule array 5 includes vestibule flask 51, dispensing-gas inlet 5-V and outlet riser 55, all arranged and operating in the manner of the embodiment of FIG. 1.

Thus, the introduction of a prescribed pumping pressure burst into storage head space 2-H (via pressure inlet 20-PV) to a prescribed degree will apply a pneumatic pressure on the surface of reagent RR, drive it up riser 2-P along conduit 5-I, through valve 53, and into vestibule flask 51 to fill and replenish it to the prescribed indicated "FULL" level, as described before. Liquid will likewise be driven up riser 2-R to the same level in level detect unit HD. Pedestal 20-P is disposed somewhat below the elevation of vestibule flask 51, but not so much as to require excessively high pumping pressures to transfer reagent therebetween.

As before, the pressurized dispensing gas is applied to vestibule flask 51 via conduit 5-V (from controlled pressurized gas source PG via valve V-5) (second pressuring means) to pressurize to reagent RR' therein, thereby seating inlet check valve 53 and driving reagent RR' out the exit riser 55, into metering vessel MV. Here it is collected until the liquid level rise in MV as detected by one of the associated photoelectric liquid level detectors DM-1, DM-2 and DM-3 located on a gauge tube G-T portion of MV+s whereupon an electrical signal, supplied via appropriate electrical circuits (not shown but well known in the art) operates valve V-5 to release pressure and apply venting to the head space in flask 51. The flow of liquid through riser 5-O stops immediately and any liquid in the line is drawn back by siphon action into the vestibule flask 51. Vestibule flask 51 is at a lower elevation than metering vessel MV to effect this back-siphoning action.

A control monitor is provided to indirectly monitor the level of liquid in vestibule flask 51 and thereby provide a continual automatic replenishment thereof from reservoir 20. Replenishment is invoked when the vestibule reagent level drops below the reference "FULL" level as detected at a level detect assembly HD', including a vessel V in hydraulic communication with transfer vessel 51 via conduit 5-I and riser 2-P. Using photosensor level detect means, or otherwise as known in the art, control signals may be developed (e.g., from detect unit D-3) and applied to a control panel CP to cause pressurizing of reservoir head space 2-H whenever the vestibule liquid level falls below a reference level (here, "FULL"). A companion "over-full" detector D-2 is similarly provided and arranged, the signals therefrom being adapted to initiate controlled venting of chamber 21 (e.g., pulsatingly, as selectively controlled in pulse width and frequency at panel CP) once the vestibule liquid level has risen to, and above, the level of detector D-2. Of course, the fluid presence detectors D-1, D-2 and D-3 are positioned at any desired appropriate levels on bypass B of detector vessel V. Similarly, an "overflow" detector D-1 is likewise provided and operated to invoke emergency venting alarm and reset conditions in the event of extreme over pressurization of the storage vessel.

Other associated apparatus in this embodiment will be apparent in purpose and function to those skilled in the art. For instance, an arrangement for supplying for gross volume storage of reagent and replenishment thereof in storage vessel 21 is supplied in the form of a storage drum D and associates selectively operable pneumatic pressurized source PG-2 removably connected thereto along with a riser and associated outlet tube D-C connecting with a fill tube 20-F entering flask 21 via seal 20-S.

Thus in summary it would be apparent to those skilled in the art that the foregoing provides a direct control of pressurization of a supply reservoir by monitoring the actual liquid level rendered as a simulated value of driving pressure (head) rather than by indirect monitoring of pressure designed to produce this head in the transfer vessel. Combined utilization of this liquid-position monitoring system with a safety shut-down arrangement and a fail-safe mode in case of over-pressurization and/or overfilling is also provided. "Shut-down" can be invoked either by overfilling (e.g. without over-pressurization) or by detect-system feature.

Further, the capacity of the system to automatically compensate for various densities of liquids handled and for different drive pressures and delivery conduits and for any gas leakage (such as at the closure and seals through the closure of the supply vessel and/or the pressurizing line 6 and associated fittings, will be appreciated.

Achievement of good control system stability over a relatively wide range of operating pressures and liquid head levels with simple, inexpensive means will be seen as desirably provided, especially when operating in a pulsed-vent mode to more simply control vent rate with solenoid valves.

Other forms of this invention will occur to those skilled in the art, for instance based on other types of liquid level sensors, such as those using floats, or thermistors, or electrical capacity.

Many modifications and variations of the present invention are possible in light of the above teachings and therefore it is to be understood that within the scope of the appended claims and the invention may be practiced other than as specifically described.

What is claimed is:

1. In an improved automatic liquid dispensing system including a closed storage vessel for holding a prescribed volume of liquid to be dispensed to a use point in selectable dosages and upon demand, said closed storage vessel having a bottom, the combination therewith of:
   an intermediate dispensing system including a closed transfer vessel hydraulically coupled between said storage vessel and said use point, said transfer vessel being designed to hold a fraction of the liquid capacity of said storage vessel;
   an automatic replenishment control means adapted to automatically control the transfer of said liquid from the storage vessel to the transfer vessel; and
   a pneumatic drive means comprising controlled gas pressurizing means and controlled gas venting means for placing a pressurized gas supply in pneumatic communication with said storage vessel sufficient to effect said replenishment in response to prescribed replenishment signals from said control means; and
   wherein said automatic replenishment control means comprises a liquid level detecting sub-system comprising a riser tube having one end terminating adjacent the bottom of said storage vessel and the other end opening to the atmosphere, a plurality of detect units for detecting the presence of liquid at a minimal and other prescribed hydraulic reference levels in said riser tube, said detect units being mounted adjacent said riser tube; wherein each unit is coupled to apply signals to manipulate said control means; and wherein some of said signals are adapted to enable said gas pressurizing means and other of said signals are adapted to enable said gas venting means.

2. The combination as recited in claim 1 wherein said detect system comprises at least three photoelectric detectors designed and arranged to generate solenoid-enabling signals, a first detector adapted to issue first signals enabling the coupling of said pneumatic drive means to said storage vessel, sufficient to drive liquid therefrom to said transfer vessel until the sensed liquid level exceeds a prescribed "near-full" level;
   a second detector adapted to issue second signals enabling the coupling of pneumatic vent means to said storage vessel when said liquid level reaches a prescribed "over-flow" level; and
   a third detector adapted to issue third signals enabling the coupling of pneumatic vent means to said storage vessel as well as invoking emergency alarm conditions and the disablement of said drive means until reset, as long as the liquid level sensed thereby exceeds a prescribed "over-flow" level.

3. An automatic liquid dispensing apparatus comprising:
- a closed storage vessel for containing a large quantity of liquid and having a bottom;
- a first pressurizing means including a valve means connected to said storage vessel for controllably pressurizing said vessel;
- a closed intermediate vessel for containing a small quantity of liquid and having a bottom, said intermediate vessel being located remote from said storage vessel;
- an inlet fluid conduit means having one end terminating adjacent the bottom of said storage vessel and the other end connected adjacent the bottom of said intermediate vessel;
- an outlet fluid conduit means having one end terminating adjacent the bottom of said intermediate vessel and the other end defining a discharge point;
- second pressurizing means connected to said intermediate vessel for periodically pressurizing said vessel to expel liquid therefrom;
- fluid control means between said intermediate vessel and said storage vessel for allowing passage of liquid from said storage vessel to said intermediate vessel when the head pressure in said storage vessel is greater than the head pressure in said intermediate vessel and restricting passage of said liquid from said intermediate vessel to said storage vessel when the head pressure in said intermediate vessel is greater than the head pressure in said storage vessel;
- a riser tube having one end terminating adjacent the bottom of said storage vessel and the other end opening to the atmosphere;
- a pair of spaced apart, liquid detecting means associated with said riser tube each generating an electrical signal in response to the liquid passing a given height in said riser tube;
- electrical circuit means connected between said pair of liquid detecting means and said valve means for pressurizing said storage vessel in response to one of said electrical signals and venting said storage vessel in response to the other of said electrical signals.

4. The automatic liquid dispensing apparatus as defined in claim 3 further comprising:
- third liquid detection means associated with said riser tube for generating a third electrical signal in response to the liquid passing a height in said riser tube indicating an over pressurized condition of said storage vessel and electrically connected to said electrical circuit means;
- said electrical circuit means operative in response to said third electrical signal for venting said storage vessel and preventing operation of said valve means in response to the other of said electrical signals until reset.

5. An automatic liquid dispensing apparatus comprising:
- a pressurizing means including a valve means connected to a storage vessel for controllably pressurizing said vessel, said storage vessel having a bottom;
- an outlet fluid conduit means having one end terminating adjacent the bottom of said storage vessel and the other end defining a discharge point;
- a riser tube having one end terminating adjacent the bottom of said storage vessel and the other end opening to the atmosphere;
- a pair of spaced apart, liquid detecting means associated with said riser tube each generating an electrical signal in response to the liquid passing a given height in said riser tube; and
- electrical circuit means connected between said pair of liquid detecting means and said valve means for pressurizing said storage vessel in response to one of said electrical signals and venting said storage vessel in response to the other of said electrical signals.

6. The automatic liquid dispensing apparatus as defined in claim 5 further comprising:
- third liquid detection means associated with said riser tube for generating a third electrical signal in response to the liquid passing a height in said riser tube indicating an over pressurized condition of said storage vessel and electrically connected to said electrical circuit means;
- said electrical circuit means operative in response to said third electrical signal for venting said storage vessel and preventing operation of said valve means in response to the other of said electrical signals until reset.

* * * * *